Feb. 27, 1962 H. C. SWIM ETAL Plant Pat. 2,132
ROSE PLANT
Filed March 30, 1961
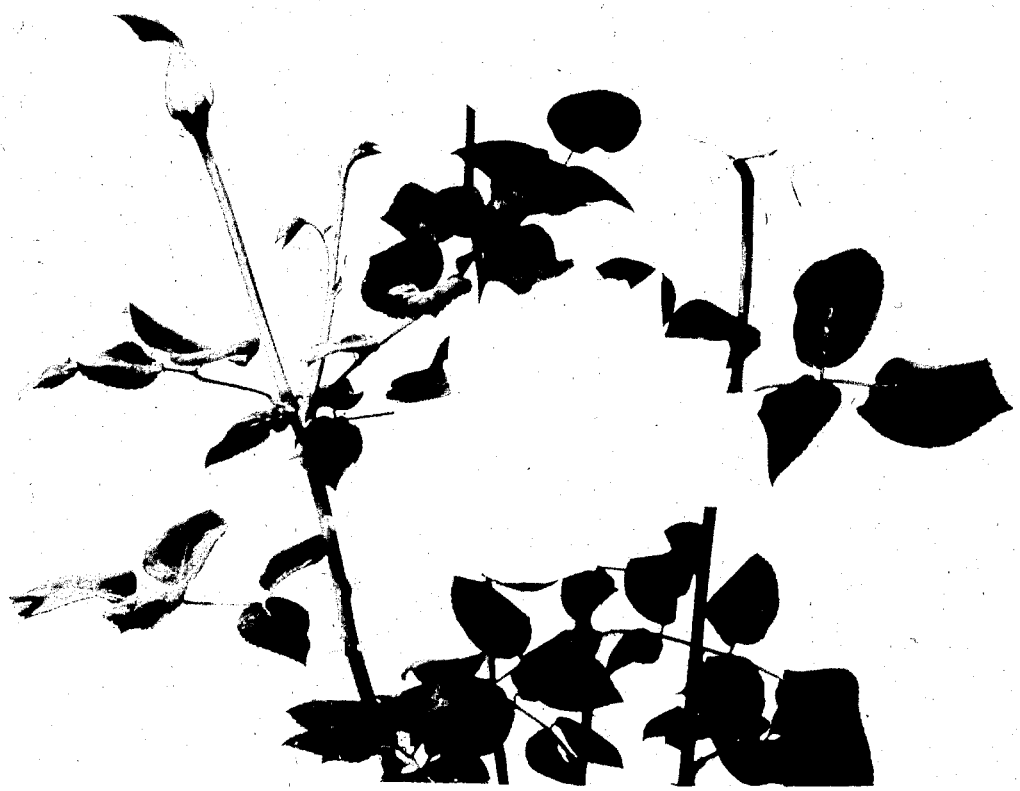
INVENTORS
H. C. Swim
O. L. Weeks
BY Robb & Robb
ATTORNEYS United States Patent Office Plant Pat. 2,132
Patented Feb. 27, 1962

2,132
ROSE PLANT

Herbert C. Swim, Ontario, and O. L. Weeks, Chino, Calif., assignors to The Conard-Pyle Company, West Grove, Pa., a corporation of Pennsylvania Filed Mar. 30, 1961, Ser. No. 99,649
1 Claim. (Cl. 47—61)

The present invention relates to a new and distinct variety of rose plant of the grandiflora class, which was originated by us by crossing the variety "Queen Elizabeth" (Plant Patent No. 1,259) with the variety "Blanche Mallerin" (Plant Patent No. 594).

As the result of this breeding, we have created a new rose variety which is endowed with the following unique and desirable combination of characteristics which are outstanding therein and which distinguish it from its parents, as well as from all other varieties of which we are aware:

(1) A vigorous, tall and erect habit of plant growth, and a habit of producing long flower stems;

(2) Heavy and leathery foliage of grey-green cast and which is quite resistant to mildew;

(3) Large buds of from long-pointed to urn-shaped form;

(4) Broad petaled flowers;

(5) A distinctive and attractive white color tonality of the flowers; and (6) Very smooth hips which become quite rounded at maturity and yellow in color.

In comparison with its seed parent "Queen Elizabeth," our new variety does not have as thick growth; the foliage is smaller and not as abundant; the color of the foliage is grey-green, as distinguished from the more yellowish green of this parent; the buds and flowers are larger and the buds are much longer and more urn-shaped than those of this parent; and the buds and flowers are white or nearly white, as distinguished from the pink buds and flowers of the parent "Queen Elizabeth."

As compared with the pollen parent "Blanche Mallerin," the new variety is very tall growing in habit, as distinguished from the more modest height of the plants of this parent; it is much more resistant to mildew under comparable conditions in southern California; the flower stems are much longer, but the plants are less thickly branched; and the flowers have fewer petals than those of "Blanche Mallerin."

Asexual reproduction of our new rose variety by budding, as performed at Chino, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Inc., of Baltimore, Maryland, except where general color terms of ordinary dictionary significance are obvious:

Type: Half-hardy; tall; bush; outdoor; seedling; for cut flowers and for garden decoration.

Class: Grandiflora.

Breeding: Seedling.

*Seed parent.*—"Queen Elizabeth."

*Pollen parent.*—"Blanche Mallerin."

Propagation: Holds its distinguishing characteristics through succeeding propagations by budding.

*Flower*

Locality where grown and observed: Chino, California.

Flowers borne: Sometimes singly and sometimes 2 or 3 to stem; in irregular cluster; on long stems of from normal strength to strong.

Quantity of bloom: From moderate to free, both outdoors and in greenhouse.

Continuity: More or less continuous.

Fragrance: Moderate. Nature—tea.

Bud:

*Peduncle.*—Long; from medium caliper to heavy; erect; smooth, except for numerous stipitate glands. Color—light green.

*Before calyx breaks.*—Size—large. Form—long; pointed; usually with foliaceous appendages on the surface of the bud; with only occasional foliaceous parts extending beyond the tip of the bud equal to ½ or more of its length. Color—near Strong Yellow Green, Plate 7.5GY 6/8, but covered with enough greyish tomentum to alter color to a more greyed hue.

*As calyx breaks.*—Color—between white and Light Yellow Green, Plate 7.5GY 9/4.

*As first petal opens.*—Size—large. Form—long; from pointed to urn-shaped. Color: outside—small area around base Brilliant Yellow Green, Plate 2.5GY 9/8, with midrib near Light Yellow Green, Plate 7.5GY 9/4 from base to ⅘ of its length, and with remainder white or very nearly so; inside—small area around point of attachment Brilliant Yellow Green, Plate 2.5GY 9/8, with midrib Brilliant Yellow Green, Plate 5GY 8/8, occasionally with hint of latter color in veins, and with remainder white or very nearly so.

*Opening.*—Opens up well.

Bloom:

*Size (when fully open).*—From 4½ inches to 5 inches.

*Petalage.*—Double; from 20 to 26 petals; arranged regularly; occasionally from 1 to 4 petaloids arranged irregularly.

*Form.*—From flat to high-centered at first, but becoming more high-centered; petals at first being loosely flat, but center petals later becoming loosely erect at maturity.

Petals:

*Texture.*—Medium thickness. Inside—satiny. Outside—satiny.

*Shape.*—Outside—very broadly obovate, with apex flat or with one notch. Intermediate—broadly obovate, with apex having blunted point. Inside—obovate; irregularly scalloped; apex not pronounced.

This description of a newly opened flower was made from a rose grown in a greenhouse during the month of February at Chino, California:

*Color.*—Outer petal: outside surface—Brilliant Yellow Green, Plate 2.5GY 9/8 at base in small area about point of attachment, with midrib slightly more greenish at base and carrying color to about midway of petal, with occasional flecks of Light Yellow Green, Plate 7.5GY 9/4 about upper margin; inside surface—small area around point of attachment Brilliant Greenish Yellow, Plate 7.5Y 9/8, fading out to white about ¾ inch from base, with remainder of petal white or nearly white. Intermediate petal: outside surface—small area around point of attachment Brilliant Greenish Yellow, Plate 10Y 9/9, with some influence of this color over lower half of petal, but otherwise white or nearly so; inside surface—Brilliant Greenish Yellow, Plate 7.5Y 9/8 near point of attachment, with some influence of this color over entire lower portion of petal, but fading to white or nearly so over upper half. Inner petal: outside surface—near Brilliant Greenish Yellow, Plate 10Y 9/9 near point of attachment, with hint of this color following midrib to central portion of petal, and with remaining portion white or nearly so; inside surface—Brilliant Greenish Yellow, Plate 7.5Y 9/8 near point of attachment, but progressively fading to white toward apex, although not attaining a pure white tone.

This description was made from a rose that was open for 3 days in a greenhouse during the month of February at Chino, California:

*Color.*—Outer petal: outside surface—a hint of unidentifiable greenish yellow color in lower portion of petal, quickly becoming white or very nearly so; inside surface—a hint of unidentifiable greenish yellow color in lower portion of petal, quickly becoming white or very nearly so. Inner petal: outside surface—a hint of unidentifiable greenish yellow color in lower portion of petal, quickly becoming white or very nearly so; inside surface—a hint of unidentifiable greenish yellow color in lower portion of petal, quickly becoming white or very nearly so.

*General color effect.*—Newly opened flower—faint unidentifiable yellow color in heart of flower, but outer edge white or very nearly so. 3-days open—white or very nearly white, except for sexual parts where they are exposed by petals.

*Behavior.*—Drop off cleanly.

*Flower longevity.*—Cut roses grown in greenhouse and kept at living room temperatures—6 days in February.

*Reproductive Organs*

Stamens: Moderate number; arranged irregularly about pistils.

Filaments: From 5 to 10 mm. long; most with anthers. Color—reddish.

Anthers: Medium-large; all open at once, or nearly so. Color—yellow.

Pollen: Abundant. Color—gold.

Pistils: Medium quantity.

Styles: Somewhat uneven; from short to medium length; medium-heavy; loosely bunched. Color—red.

Stigma: Color—from white to colorless.

Ovaries: All enclosed in hip, except for only a very occasional one.

Hips: Globular; very smooth; walls thick and fleshy. Color—yellow, at maturity.

Sepals: Moderately short; from straight to recurved; permanent.

Seeds: Many; large.

*Plant*

Foliage:

*Leaves.*—Compound of 3 to 5 leaflets; from moderately sparse to normal abundance; medium size; moderately heavy; leathery.

*Leaflets.*—Shape—ovate, with apex acute to acuminate. Base—rounded to slightly but unevenly lobed. Margin—both simply and doubly serrate.

*Color.*—mature: upper surface—between Dark Yellowish Green, Plate 2.5G 3/3 and Moderate Olive Green, Plate 7.5GY 4/4, with veins of strong Yellow Green, Plate 7.5GY 7/9; under surface—network of veins near Moderate Olive Green, Plate 7.5GY 4/4, with midrib and its main branches and inter-veinal areas covered with whitish tomentum to give a greyish cast to these areas. Young: upper surface—near Moderate Olive Green, Plate 2.5GY 4/3, except for margin which is heavily tinged with anthocyanin; under surface—main veins remain greenish, but remainder heavily stained with anthocyanin.

*Rachis (the supporting stem of the compound leaf.*—From light to medium weight. Upper side—grooved; margins lined with stipitate glands. Under side—sparsely prickly; moderately glandular.

*Stipules.*—Moderately short; narrow; with short points recurved toward the stem.

*Disease resistance.*—Very resistant to mildew as compared with other white varieties of the hybird tea or grandiflora classes, when grown under comparable cultural conditions and climate at Chino, California.

Growth:

*Habit.*—Tall; upright; moderately branched.

*Growth.*—From moderate to very vigorous.

*Canes.*—Medium caliper; exceptionally long for this type.

*Main stems.*—Color—grey-green. Large prickles—several; medium length; straight; with short, broad base; color—brown. Small prickles—few; color—brown. Hairs—none.

*Branches.*—Color—grey-green. Large prickles—several; medium length; straight; with short, broad base; color—brown. Small prickles—few; color—brown. Hairs—none.

*New shoots.*—Color—yellow-green. Large prickles—several; medium length; straight; with short, broad base; color—light yellow-green, with base encircled with anthocyanin. Small prickles—few; color—green, with base encircled with anthocyanin. Hairs—none.

We claim:

A new and distinct variety of rose plant of the grandiflora class, substantially as herein shown and described, characterized particularly as to novelty by the unique combination of a vigorous, tall and erect habit of plant growth, long flower stems, heavy, leathery leaves of grey-green cast which are quite resistant to mildew, large, long-pointed to urn-shaped buds, broad petaled flowers, a white general color tonality of the flowers, and very smooth hips, which become quite rounded and yellow in color at maturity.

No references cited.